Figure 1:
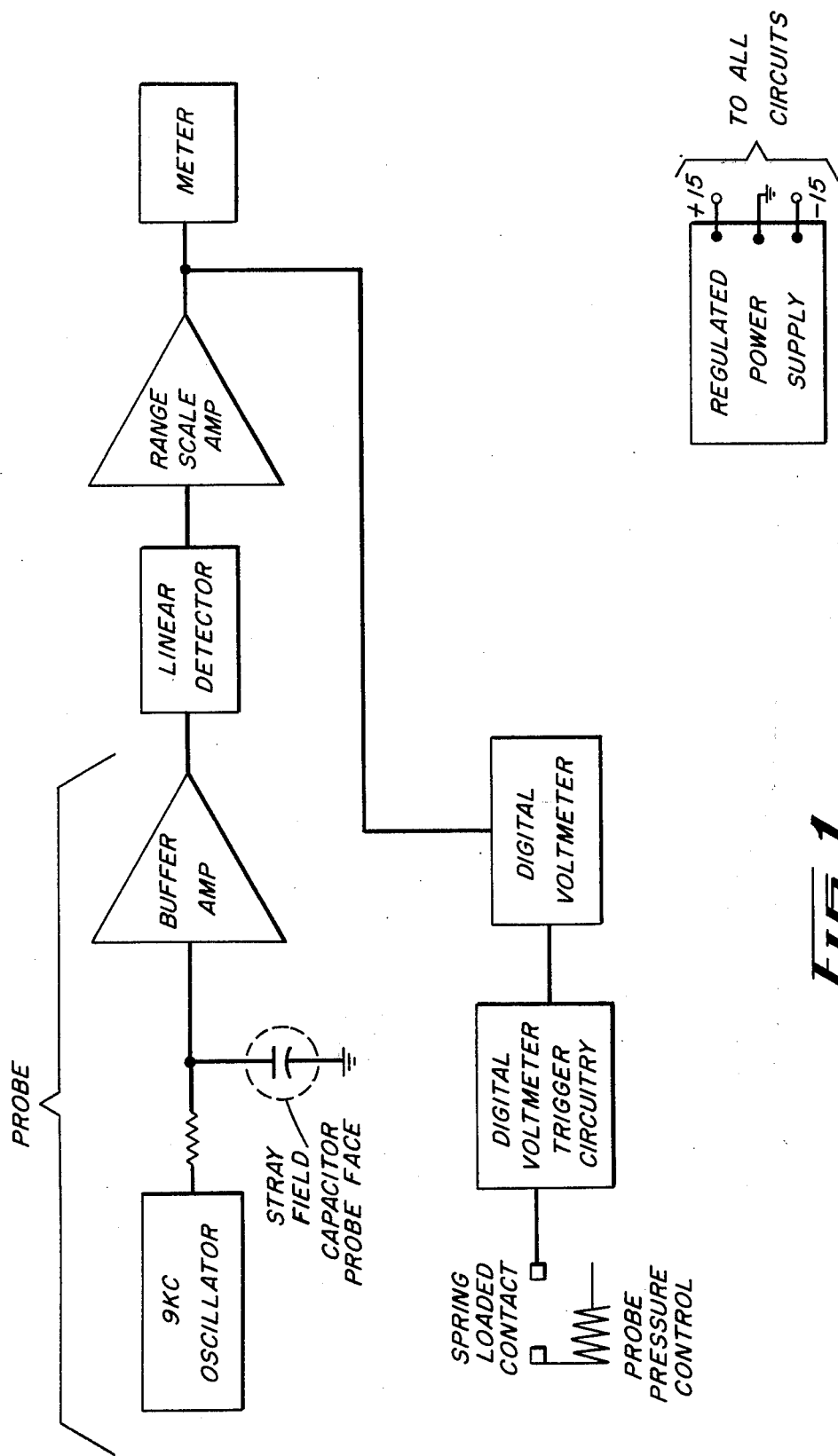

United States Patent [19]

Copeland et al.

[11] 4,013,065
[45] Mar. 22, 1977

[54] MOISTURE DERMATOMETER

[75] Inventors: Melvin Copeland, Nanuet; William Peter Konazewski, South Spring Valley, both of N.Y.

[73] Assignee: American Cyanamid Company, Stamford, Conn.

[22] Filed: Feb. 23, 1976

[21] Appl. No.: 660,591

[52] U.S. Cl. .................................. 128/2 R; 73/73; 128/2.1 R
[51] Int. Cl.² ......................................... A61B 5/05
[58] Field of Search ............ 128/2 R, 2.1 R, 2.1 Z; 73/73, 74

[56] References Cited

UNITED STATES PATENTS

| | | | |
|---|---|---|---|
| 2,076,441 | 4/1937 | Berry | 128/2.1 R X |
| 2,941,174 | 6/1960 | Richards | 73/73 X |
| 3,713,966 | 1/1973 | Lippke | 73/73 X |

Primary Examiner—Kyle L. Howell
Attorney, Agent, or Firm—Charles J. Fickey

[57] ABSTRACT

A device to measure the moisture content of the stratum coreum of human skin by means of a stray field capacitor, including means to process, and display a quantitative reading from the stray field capacitor measurement.

6 Claims, 6 Drawing Figures

MOISTURE DERMATOMETER

This invention relates to the measurement of moisture in a substrate and to a device for making such measurements. More particularly, the invention relates to a moisture dermatometer, that is a device for measuring the moisture content of human skin (the stratum coreum). For cosmetic or other purposes, it is desirable to be able to determine the moisture in the skin. The measurement of the moisture content of the stratum corneum requires an instrument which is sensitive over a small range of skin depth. The stratum corneum is surrounded on one side by the outside environment with relatively low moisture content, and on the other side by the deeper layers of the skin with much higher moisture content.

The ideal instrument should sense moisture only in this narrow region. The moisture dermatometer, which uses the principle of a "stray field capacitor", most nearly meets these requirements.

It is an object of this invention, therefore, to provide a device which will accurately measure the moisture content of the stratum coreum of the human skin.

This and other objects of the invention will become apparent as the description thereof proceeds.

The present device makes use of a stray field capacitor.

A capacitor is a device that consists essentially of two electrical conductors separated by an insulator or dielectric. If a charge of electrons or an electric potential is placed across these conductors, an electric field will be developed accross the insulator. Most of the flux lines and therefore most of the field is essentially perpendicular from conductor to conductor. Near the ends of the conductor there is some curvature of the flux lines. Beyond the end of the conductors the number of flux lines and consequently the field strength diminishes rapidly. The range of this fringe field is determined to a major extent by the spacing of the conductors. The closer the spacing, the closer the fringe or stray field. It is essentially these properties of the stray field that are used in the moisture dermatometer.

In an alternating current circuit a capacitor acts to control the amount of current flowing through it. The greater the capacitance, the greater the current that will flow.

The magnitude of the capacitance is inversely proportional to the spacing of the conductors and proportional to the cross-sectional area of the conductors and the dielectric constant of the insulator or dielectric. The dielectric constant is a measure of polarizability of the atoms or molecules in the insulator. The greater the value of the dielectric constant of the material between and near the conductors, the greater the capacitance.

The face of the dermatometer probe contains a capacitor which is formed by two copper conductors. These conductors are photoetched in an interleaved or interdigitated pattern to increase the number of facing surfaces, and therefore the total capacity or sensitivity of the instrument. After etching, the face of the probe is coated with a thin coating of an epoxy plastic which electrically insulates the surface of the probe.

If an alternating current is applied to this capacitance, most of the field will be between the conductors and will not penetrate the epoxy insulator. A small portion of this field will however penetrate the epoxy insulator and extend a short distance beyond the surface of the probe. The particular dielectric material that this stray field encounters will affect the capacitance value of the probe. Water with a dielectric constant around 80 will produce a much greater increase in capacity than air with a dielectric constant near 1. Skin will produce intermediate readings.

Basically, it is the modification of the probe capacity by the dielectric constant of the material in the stray field that is the detecting principle of this instrument.

The electronic circuitry provides the means for detecting this change of capacity and presenting it as a calibrated meter reading.

Several state-of-the-art- integrated circuits are incorporated into the electronics to provide circuitry that is accurate and sophisticated but still compact.

The invention may be better understood by reference to the drawings in which:

FIG. 1 is a block diagram of the components of the moisture dermatometer

Figure 1A:
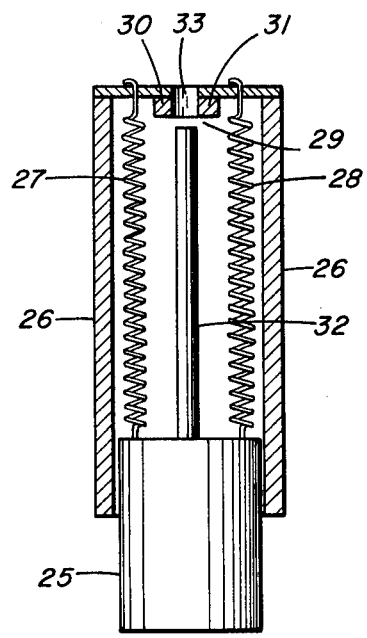
Figure 1B:
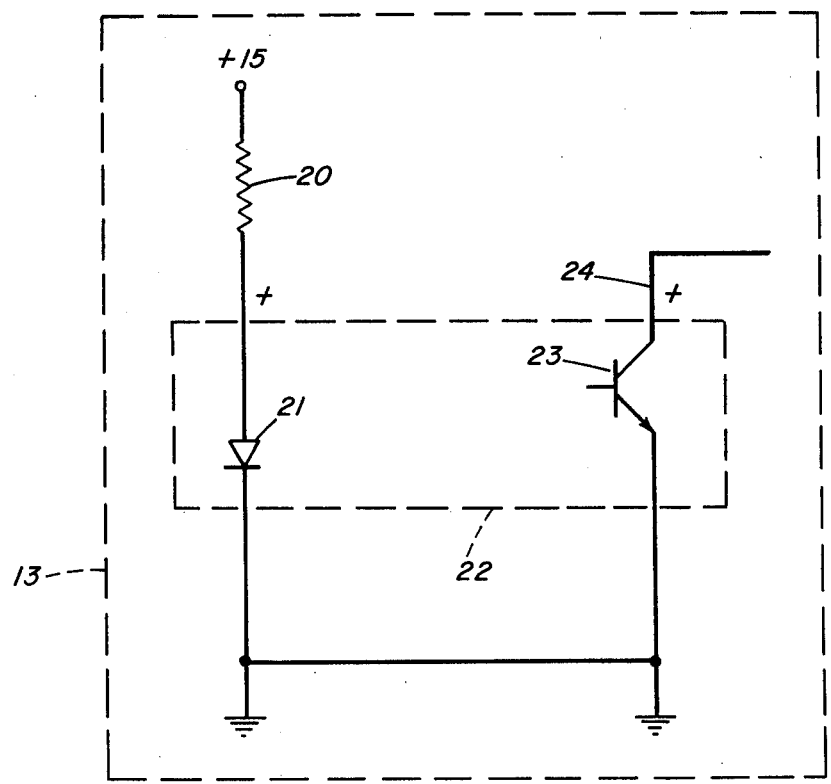
Figure 2:
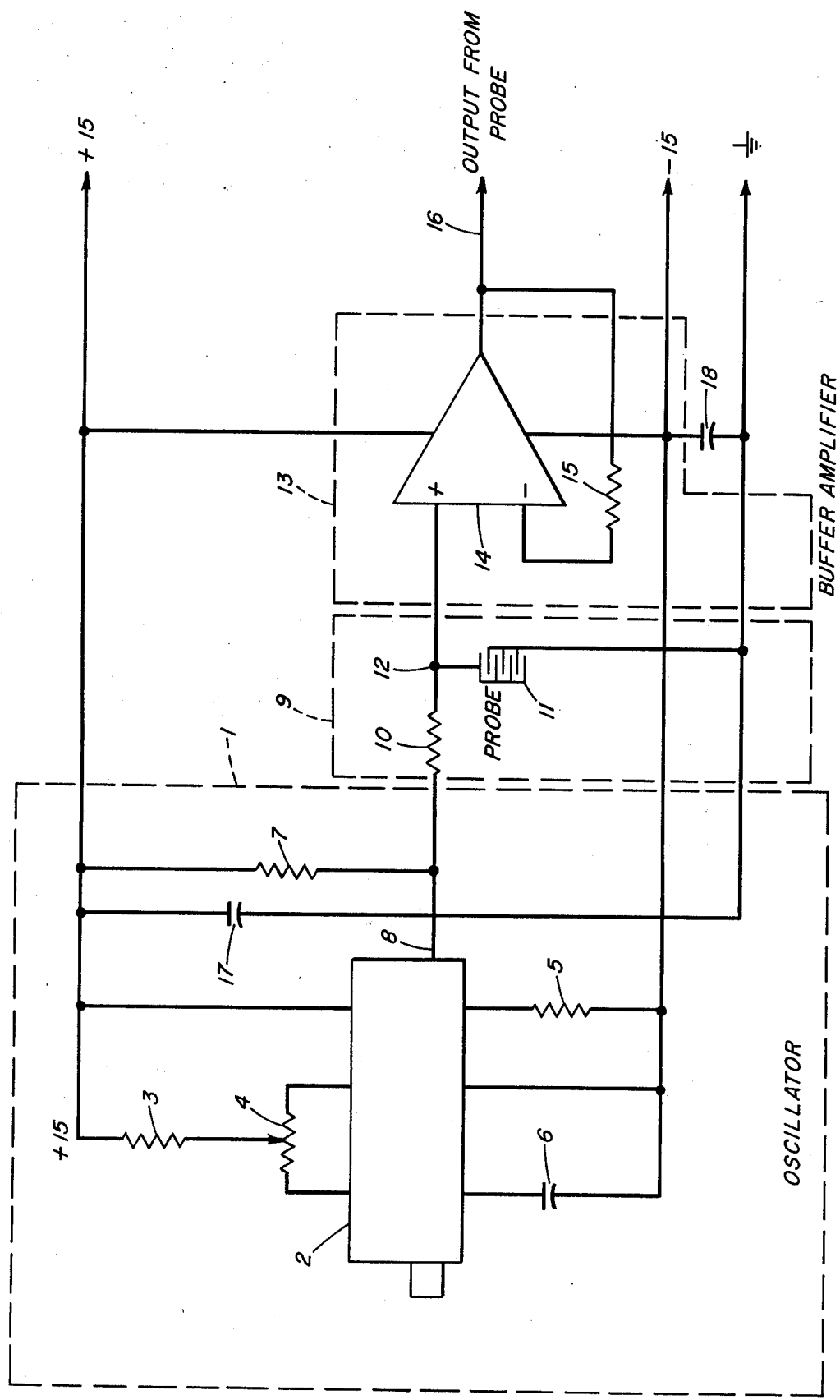
Figure 3:
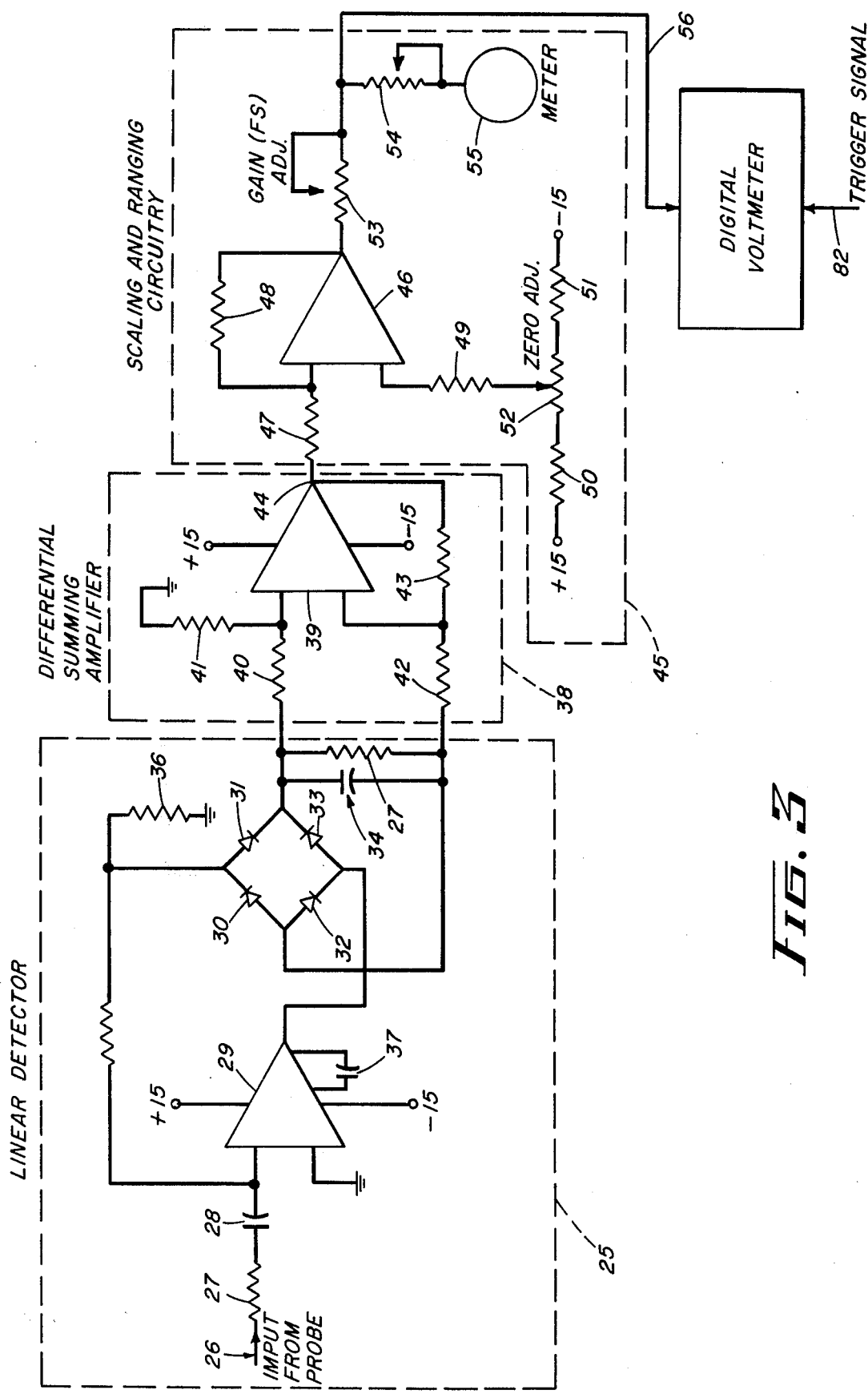
Figure 4:
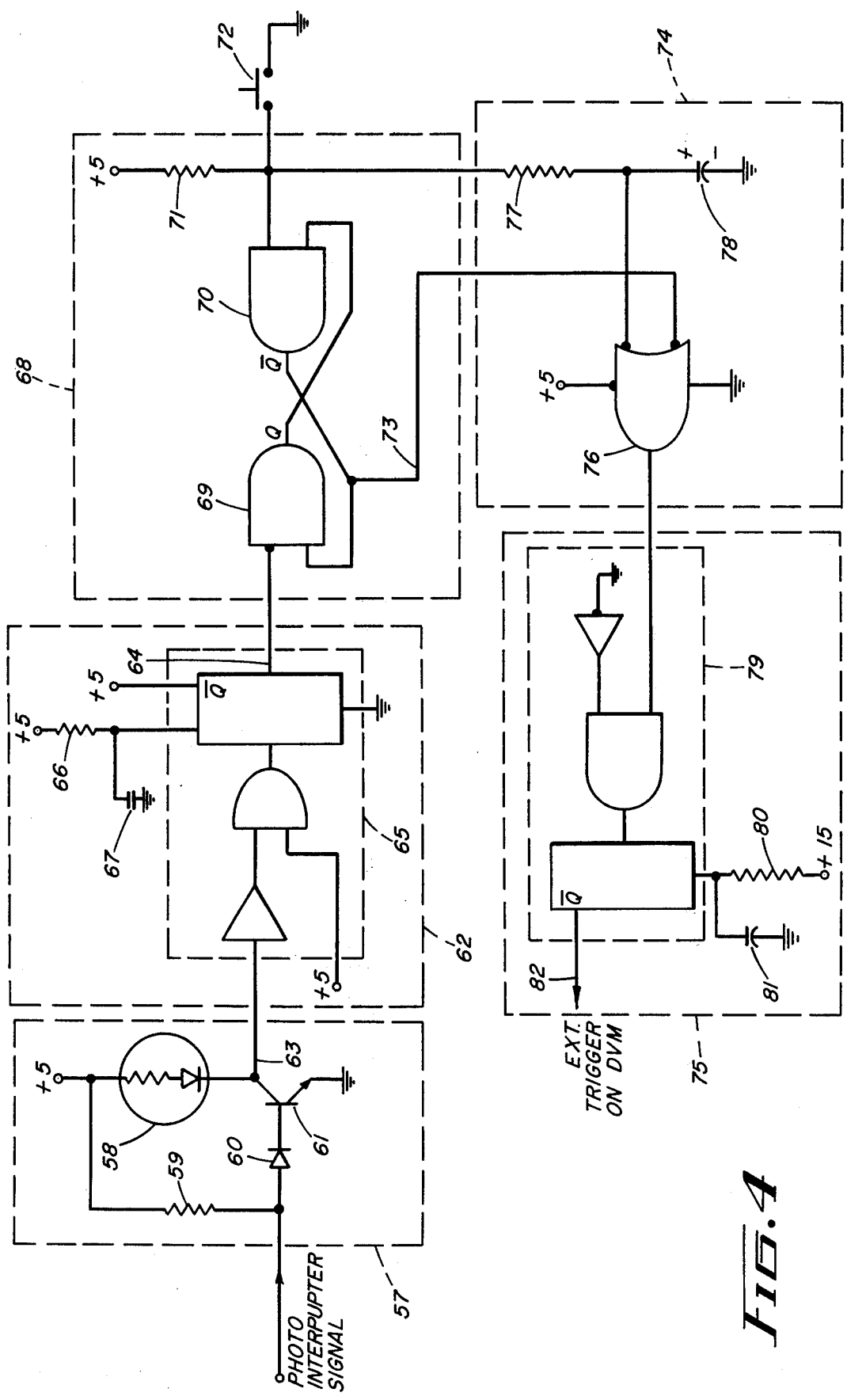

FIG. 1A is a digramtic illustration of the mechanical features of the dermatometer probe, FIG. 1B is a diagram of the interrupter circuitry of the probe, FIG. 2 is a detailed circuit diagram of the probe, FIG. 3 is a diagram of the circuitry for processing the electrical signal from the probe, and FIG. 4 is a diagram of the circuitry for producing a trigger signal to fix the reading time measurement.

Referring to FIG. 1, the signal source is provided by an integrated circuit which provides a 9 kilohertz sinusoidal constant voltage output. This signal is fed through a 1 megohm resistor to the probe face capacitor. The resistor and the capacitor form a voltage divider for the oscillator output with the junction forming the pickup point for further signal processing. stray field causes an increase in probe capacity and an increase in current in the series circuit formed by the resistor and the probe capacitor. This increased current causes a greater voltage drop across the resistor and a lower voltage at the junction of the resistor and capacitor. This change in voltage is the transduced signal output used for developing the output meter reading.

The resistor and probe circuit form a high impedance circuit. Care must be taken to avoid loading this circuit and introducing sources of error. This is accomplished by using a FET input buffer amplifier which has very high input resistance and very low input capacitance. the oscillator, resistor and buffer amplifier are all incorporated within the probe to avoid loading and noise pickup. The buffer amplifier provides a low impedance output which is insensitive to noise. The buffer amplifier output is fed via a shielded cable and connector into an instrument cabinet, not shown.

The instrument cabinet contains: the balance of the processing circuitry, a regulated power supply that renders the instrument insensitive to line voltage fluctuations, a meter and controls for zeroing and calibrating the meter, a power switch, a digital voltmeter for digital readout, and a triggering circuit for the digital readout.

The probe incorporates a spring loading mechanism which closes an electrical contact when the proper force is attained.

Referring to FIG. 2, showing the probe circuitry in greater detail, the probe contains an oscillator circuit 1 consisting of an integrated circuit waveform generator 2 which produces a 9,000 hertz sine wave with low distortion. Resistor 3 is used to adjust the frequency of the oscillation and potentiometer 4 is a waveform-symmetry adjustment. Resistor 5 is selected to minimize sine wave distortion. Capacitor 6 is a timing capacitor. Resistor 7 is a load resistor.

The oscillator output 8 is connected to the transducer circuit 9. Resistor 10 and capacitance sensor 11 form a voltage divider for the oscillator output with the junction 12 forming the pickup point for further signal processing.

An increase in the dielectric constant within the stray field of the probe causes an increase in probe capacity and an increase in current in the series circuit formed by resistor 10 and capacitance sensor 17. This increased current causes a greater voltage drop across resistor 10 and a lower voltage at point 12. This change in voltage is the transduced signal output used for developing the output meter reading.

Mechanical and dimensional construction on the probe result in a high impedance circuit. Care must be taken to avoid loading this circuit and introducing noise and other sources of error. This is accomplished by connecting the signal at 12 to a buffer amplifier circuit 13 which has very high imput resistance and very low input capacitance. The oscillator 1 transducer 9, and buffer amplifier 13 are all incorporated within the probe to avoid loading and noise pickup.

The buffer amplifier contain a field-effect transistor input integrated circuit operational amplifier 14 and feedback resistor 15 which provides a circuit with unity voltage again. The buffer amplifier provides a low impedance output at 16 which is insensitive to noise. This output is fed via shielded cable and connects to the instrument cabinet.

The probe operates off regulated positive and negative voltages obtained through the connecting cable from the instrument cabinet. Capacitors 17 and 18 are used to decouple noise on the power supply lines.

Also incorporated within the probe is a mechanism which optimizes the accuracy of the system by insuring that all readings are taken with a constant force applied to the probe.

The probe tip 25 with stray field capacitor 11 slides within the barrel 26 (see FIG. 1A) and is restrained by two compression springs 27 and 28.

A photointerrupter 29 is attached to the rear of the barrel. The photointerrupter consists of a light emitting diode 30 and phototransistor 31 separated by an air gap. Without an object in the gap the light from the light emitting diode is coupled to the phototransistor turning the phototransistor on. Attached to rear of the probe tip is an adjustable slug 32 which under the proper spring compression blocks the gap between the light emitting diode and the photo-transistor turning the phototransistor off. Pressure adjustment is attained by turning slug 32 through access hole 33 in the rear of the barrel.

Electrically, the photointerrupter circuit is shown in 19 (see FIG. 1B). Resistor 20 establishes the current level in the light emitting diode 21 which is part of photo-interrupter 22. The collector output 24 of phototransistor 23 is coupled to the instrument cabinet via the shielded connecting cable. The collector output presents a low voltage signal when the probe is not compressed and a higher voltage when the proper force is reached.

An instrument cabinet, not shown, contains the regulated power supplies, digital and analog meters which indicate the skin moisture, a connector for the external probe, controls for calibrating and operating the instrument and circuiting for processing the signal outputs of the probe and providing the proper information to the displays.

FIG. 3 shows the circuitry for the meter displays and FIG. 4 shows the circuitry that triggers the digital voltmeter when the proper probe force is attained.

Referring to FIG. 3, the transduced output signal from the probe buffer amplifier comes into the linear detector circuit 25 at the input 26. The linear detector circuit provides a direct current output at resistor 27 which is proportional to the amplitude of the 9,000 hertz signal at the input. The circuit consists of an integrated circuit operational amplifier 29 and a diode bridge containing diodes 30, 31, 32 and 33 in the feedback path. The diodes steer the signal to provide negative feedback for the amplifier, but a positive or direct current output across resistor 27.

Capacitor 34 acts as a low pass filter to remove any ripple on the direct current output. Resistor 35 serves as a feedback resistor. Resistor 36 serves as a load resistor. Capacitor 37 is a compensation capacitor to prevent oscillation of the operational amplifier.

The voltage across resistor 27 appears as an input to differential summing amplifier 38. The circuit consists of an integrated circuit operational amplifier 39 and scaling and feedback resistors 40, 41, 42 and 43. The summing amplifier presents a single ended output at 44.

The summing amplifier output 33 is presented to the scaling and ranging circuitry 45 which provides the circuitry and and controls to calibrate the instrument and provide the proper meter presentations. The circuit consists of an integrated circuit operational amplifier 46, gain control and feedback resistors 47 and 48, input matching resistor 49, zero bias resistors, 50 and 51 and zero adjust potentiometer 52. Rheostat 53 serves as a gauge or full scale adjustment and rheostat 54 serves to scale the output of the analog meter 55 to that of the digital voltmeter output 56. The instrument is calibrated to provide a zero reading with the probe in air and an arbitrary full scale reading of 80 with the probe tip immersed in distilled water.

Another portion of the circuitry in the instrument cabinet turns on a light emitting diode indicator and triggers a digital voltmeter reading when the proper probe force is attained.

The signal from the photointerrupter 24 (see FIG. 1B) is applied to the input circuit 57 (see FIG. 4). This circuit provides amplification to drive the light emitting diode indicator 58 and trigger the "one-shot" circuit 62. The input circuit contains bias resistor 59 and bias diode 60 and transistor 61.

The output of the input circuit at 63 provide a low output signal when the slug in the probe blocks the photo-interrupter. This high to low voltage transistor triggers the one-shot circuit to provide an output pulse at 64 to provide a pulse which goes from a quiescent high level down to a low level and back to a high level. The one-shot circuit consists of an integrated circuit one shot 65, timing resistor 66 and timing capacitor 67.

The output pulse of the one-shot circuit sets the "Q" output of the "latch" circuit to a high level and the $\overline{Q}$ (Q-nor) output to a low level. The latch circuit consists of two cross-connected integrated circuit gates 69 and 70 and bias resistor 71. After a reading the latch circuit is reset to its initial state by momentarily depressing push-button switch 72.

The high-to-low transistor of $\overline{Q}$ output 73 is applied to "or-gate" circuit 74. This or gate circuit allows the $\overline{Q}$ transition or the reset to trigger the output one shot circuit 75. The or-gate circuit consists of an integrated circuit gate 76 and resistor 77 and capacitor 78 delay circuit which prevents a "race" condition with the latch output.

The output one shot circuit consisting of integrated circuit one-shot 79 timing resistor 80 and timing capacitor 81. the one-shot circuit provides a pulse 82 to trigger a reading on the digital-voltmeter.

We claim:

1. A device for measuring moisture in a moist substrate which comprises, a stray field capacitor for making contact with said substrate, means to provide an oscillating signal to said stray field capacitor, and means to detect and read a modified signal produced by said stray field capacitor in contact with said moist substrate, said stray field capacitor comprising yieldable means to urge it against the skin under pressure, said means further comprising means to trigger said read means at a predetermined pressure.

2. A device as in claim 1 for measuring the moisture content of the stratum coreum of human skin wherein said stray field capacitor is adapted to make contact with the skin surface.

3. A device as in claim 2 wherein said read means is a digital voltmeter.

4. A device as in claim 2 wherein said read means is an ammeter.

5. A device as in claim 2 wherein said detecting means includes means to amplify said detected modified signal.

6. A device as in claim 5 comprising means to calibrate said signal to obtain predetermined readings for water and the absence of water.

* * * * *